(12) United States Patent
Lee et al.

(10) Patent No.: US 10,420,936 B2
(45) Date of Patent: Sep. 24, 2019

(54) ELECTRICAL STIMULATION SYSTEM

(71) Applicant: YBRAIN INC., Seoul (KR)

(72) Inventors: Kiwon Lee, Daejeon (KR); Kyongsik Yun, Daejeon (KR); Seungyeon Kim, Seoul (KR)

(73) Assignee: YBRAIN INC., Seoul (KR)

( * ) Notice: Subject to any disclaimer, the term of this patent is extended or adjusted under 35 U.S.C. 154(b) by 0 days.

(21) Appl. No.: 15/904,662

(22) Filed: Feb. 26, 2018

(65) Prior Publication Data

US 2018/0178009 A1     Jun. 28, 2018

Related U.S. Application Data

(62) Division of application No. 14/745,359, filed on Jun. 19, 2015, now Pat. No. 10,265,524.

(30) Foreign Application Priority Data

Jun. 20, 2014   (KR) .................. 10-2014-0075855

(51) Int. Cl.
    *A61N 1/36*      (2006.01)
    *A61N 1/04*      (2006.01)

(52) U.S. Cl.
    CPC ....... *A61N 1/36025* (2013.01); *A61N 1/0492* (2013.01)

(58) Field of Classification Search
    CPC ................. A61N 1/0492; A61N 1/36025
    See application file for complete search history.

(56) References Cited

FOREIGN PATENT DOCUMENTS

| KR | 20080107961 A | 12/2008 | |
|---|---|---|---|
| KR | 101094350 B | 12/2011 | |
| KR | 101473456 B1 | 10/2014 | |
| WO | WO-2014130960 A1 * | 8/2014 | ........... A61B 5/0006 |

OTHER PUBLICATIONS

Korean Office Action dated Aug. 27, 2014 for corresponding Korean Application No. 10-2014-0075855.

* cited by examiner

*Primary Examiner* — Amanda K Hulbert
(74) *Attorney, Agent, or Firm* — Studebaker & Brackett PC (57) ABSTRACT

The present disclosure relates to an electrical stimulation system, comprising, in accordance with one exemplary embodiment of the present invention, an analysis portion recognizing a brain activation pattern of a first user by analyzing a brainwave signal of the first user measured by a first electrical stimulation apparatus; and a stimulating portion applying an electrical stimulation to the brain of a second user on the basis of the information on the recognized brain activation pattern of the first user, wherein the first electrical stimulation apparatus includes a detecting portion detecting the second user's approach.

4 Claims, 7 Drawing Sheets

ELECTRICAL STIMULATION SYSTEM

CROSS-REFERENCE TO RELATED APPLICATION

This present application is a divisional application of a pending U.S. patent application Ser. No. 14/745,359 filed on Jun. 19, 2015, which claims the priority of the Korean Patent Application No. 10-2014-0075855, filed on Jun. 20, 2014 in the Korean Intellectual Property Office (KIPO), and all the benefits accruing therefrom under 35 U.S.C. § 119, the contents of which in their entirety are herein incorporated by reference.

TECHNICAL FIELD

The present invention is related to an electrical stimulation system and method, and more particularly, related to an electrical stimulation system and method which recognize the brain activation pattern of a user on the basis of a user's brainwave signal, and provide electrical stimulation to the other user on the basis of the information on the recognized brain activation pattern.

BACKGROUND ART

The brain is the highest nucleus organ of the nervous system, placed in the head. The brain consists of cerebrum, cerebellum, midbrain (mesencephalon), pons, and medulla, and generates brainwaves. The brainwave, as also known as electroencephalography (EEG), is a current of electricity generated in the course of transmission of signals between the brain nerves in the nervous system. The brainwave differs depending on the information the brain processes, and is the most important indicator for measuring brain activity.

Applying electrical stimulation to brain may help relieve or alleviate neurological symptoms such as hand tremor. There are invasive and noninvasive methods for electrical stimulation of the brain. The invasive method is to insert an electrode to the brain and to transmit the electrical signal to the electrode. On the other hand, the noninvasive method is to attach the electrode to scalp and to transmit the electrical signal to the electrode.

The noninvasive electrical stimulation has an advantage of lower cost and risk than the invasive method. Accordingly, research and development about the noninvasive electrical stimulation of the brain has been carried out.

RELATED ART DOCUMENT

Patent Document (Patent 1) Korean Patent No. 10-10094359 (Title of Invention: Multiple Bio-stimulation check analysis system, Dec. 8, 2011)

DISCLOSURE OF INVENTION

Technical Problem

The present invention seeks to provide an electrical stimulation system and method wherein the brain information processing and brain activation pattern of the user are recognized on the basis of the brainwave signal of the user, and the electrical stimulation on the basis of the information on the recognized brain activation pattern can be applied to be used for another user's brain.

Advantageous Effects

Since it is possible activating the brain condition of another user as similar as that of a user, same effect with the displacement of one user's emotion to the other can be achieved.

BEST MODE OF CARRYING OUT THE INVENTION

A desirable exemplary embodiment of the present invention will be described in detail hereinafter in reference with the accompanied drawings. The advantage and characteristic, and a method to achieve them will be obvious upon detailed description of the exemplary embodiments as well as accompanied drawings which follow. However, the present invention is not limited to the exemplary embodiments set forth herein, but can be embodied in many different forms. The exemplary embodiments are provided only to render the present disclosure complete and the scope of the present invention comprehensible to those having ordinary skill in the art. The present invention is only to be defined by the claims. A same reference mark used refers to a same element throughout the description.

Without separate definitions, all terms (including technical and scientific terms) used in the present description may be used for the meanings commonly understandable to those having ordinary skill in the art. In addition, the terms generally used and having definitions in dictionary, unless otherwise defined obviously in particular, should not be ideally or exaggeratedly interpreted.

The terms used in the present description are to explain the exemplary embodiments, not to limit the present invention thereto. In the present description, a singular form of word also includes a plural form thereof unless otherwise noted. The term "comprises" and/or "comprising" is not excluding the meaning that one or more elements other than the said element may exist or be added.

Below, the exemplary embodiments of the present invention will be explained in reference with the accompanying drawings. Each reference numeral is used consistently throughout the drawings.

Figure 1:
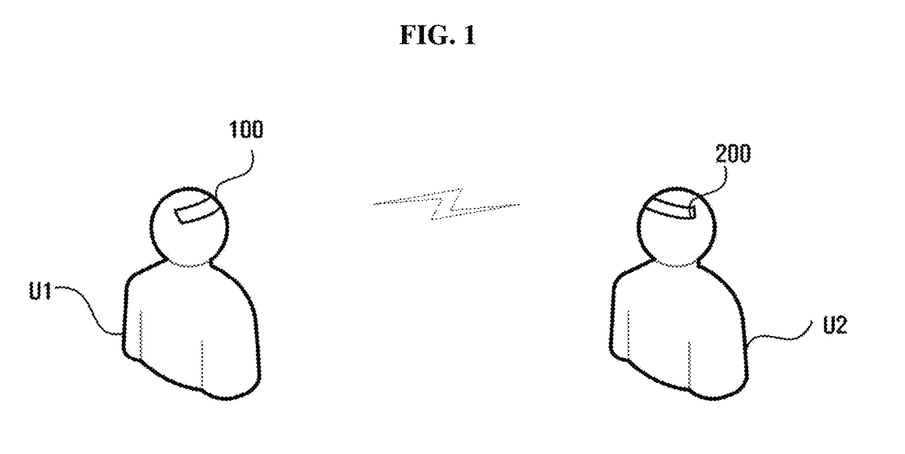
FIG. 1 is a diagram illustrating a composition of electrical stimulation system according to one exemplary embodiment.

FIG. 1 is a diagram illustrating a composition of electrical stimulation system according to one exemplary embodiment.

According to FIG. 1, the electrical stimulation system may include a first electrical stimulation apparatus (100) and a second electrical stimulation apparatus (200). At this, the first electrical stimulation apparatus (100) is an apparatus to be worn on a part of a first user (U1)'s body. The second electrical stimulation apparatus (200) is an apparatus to be worn on a part of a second user (U2)'s body. The first and second electrical stimulation apparatus (100) (200) may have a same composition. Thus, the explanation which follows will be mainly about the first electrical stimulation apparatus (100).

The first electrical stimulation apparatus (100), contacted to a certain part of the first user (U1)'s body such as a head, can measure brainwave signal or apply electrical stimulation to the brain. In order for this, the first electrical stimulation apparatus (100) can be a form wearable in the head such as a helmet. For example, the first electrical stimulation apparatus (100) can be a form of helmet. For another example, the first electrical stimulation apparatus (100) can be a form of band surrounding an entire or a part of the circumference of head. For another example, the first electrical stimulation apparatus (100) can be a form of patch adhering to scalp. However, the form of the first electrical stimulation apparatus (100) is not limited to the above examples. The composition of the first electrical stimulation apparatus (100) will be described thereinafter in reference with FIG. 2.

The first electrical stimulation apparatus (100) can measure the brainwave signal of the first user (U1) in case the first user (U1) recognizes the second user (U2). At this, the meaning the first user (U1) recognizes the second user (U2) is that the first user (U1) sees the second user (U2). According to one exemplary embodiment, the first electrical stimulation apparatus (100) can detect the second user (U2) entering within a certain range of distance from the first electrical stimulation apparatus (100). As such, when the second user (U2) is detected by the first electrical stimulation apparatus (100), it can be regarded as the first user (U1)'s recognition of the second user (U2).

After measured the brainwave signal of the first user (U1), the first electrical stimulation apparatus (100) can recognize the brain activation pattern of the first user (U1) by analyzing the measured brainwave signal. The information of the recognized brain activation pattern can be displayed on the first electrical stimulation apparatus (100) or transmitted to the second electrical stimulation apparatus (200).

The second electrical stimulation apparatus (200) can display the information of the brain activation pattern received from the first electrical stimulation apparatus (100), or apply the electrical stimulation corresponding to the information of the brain activation pattern to the brain of the second user (U2).

The explanation above was about the case the first electrical stimulation apparatus (100) recognizes the brain activation pattern of the first user (U1) by measuring the brainwave signal of the first user (U1) on detection of the second user (U2) approaching. However, the opposite case may also be possible; when the second electrical stimulation apparatus (200) detects the first user (U1) approaching, it is possible the second electrical stimulation apparatus (200) recognizes the brain activation pattern of the second user (U2) by measuring the brainwave signal of the second user (U2).

Figure 2:
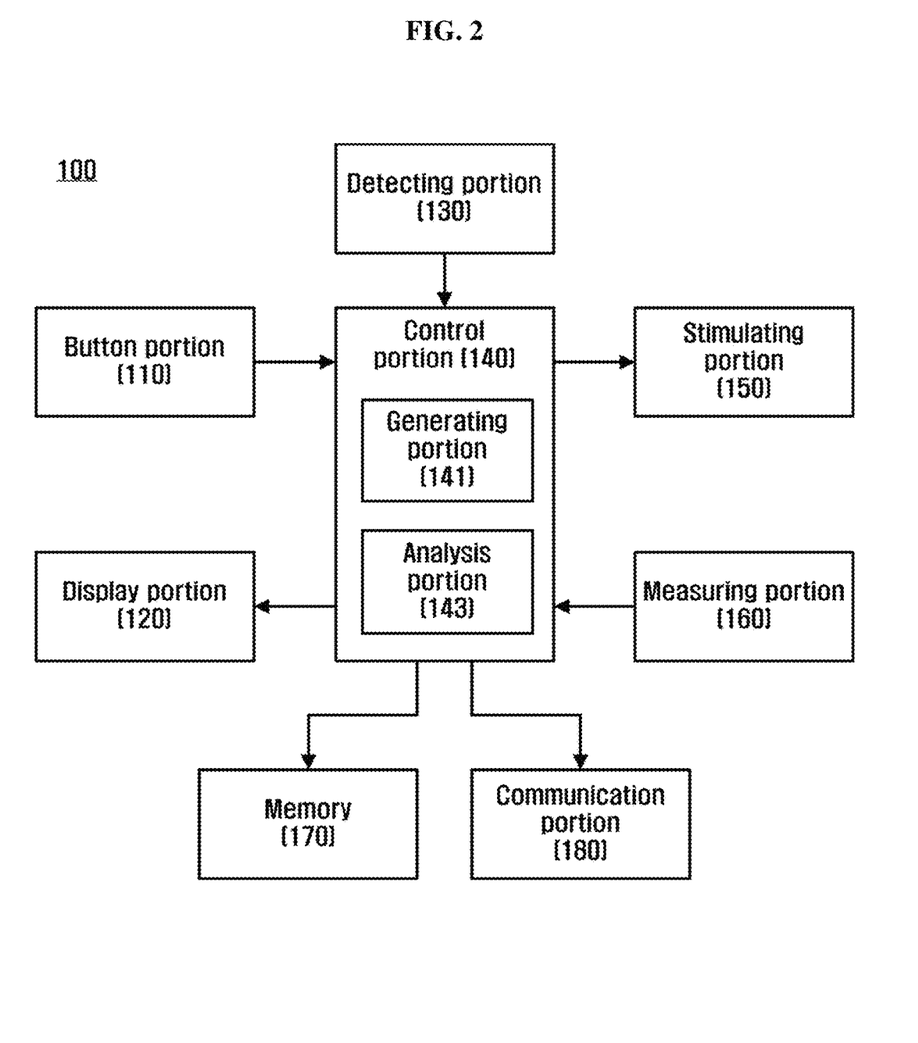
FIG. 2 is a diagram illustrating a composition of the first electrical stimulation apparatus (100) of FIG. 1.

FIG. 2 is a diagram illustrating a composition of the first electrical stimulation apparatus (100) of FIG. 1.

In reference with FIG. 2, the first electrical stimulation apparatus (100) may include a button portion (110), a display portion (120), a detecting portion (130), a control portion (140), a stimulating portion (150), a measuring portion (160), a memory (170), and a communication portion (180).

A button portion (110) enables the first user (U1) to enter command. In order for this, the button portion (110) may include at least one button. For example, the button portion (110) may include at least one selected between a power supply button and a brainwave measuring execution button, however the example is not limited thereto.

A display portion (120) can display the result of processing command. For example, the display portion (120) can display the information on the brain activation pattern of the first user (U1). For another example, the display portion (120) can display the information on the brain activation pattern of the second user (U2) received from the second electrical stimulation apparatus (200). Such display portion (120) may include at least one selected from the group consisting of a LED (Light emitting diode), a LCD (Liquid crystal display), and a flexible display.

A detecting portion (130) can detect the second user (U2) approaching to the first electrical stimulation apparatus (100). In order for this, the detecting portion (130) may include a sensor. For example, the detecting portion (130) may include a distance sensor which recognizes an object within a certain range of distance from the sensor. For another example, the detecting portion (130) may include a motion detecting sensor. However, the detecting portion (130) is not limited to the exemplified sensors, but can be embodied with different kinds of sensors. The result of detection by the detecting portion (130) can be used as an event signal to notify the start of measuring the brainwave signal of the first user (U1).

A measuring portion (160) can measure the brainwave signal of the first user (U1). In order for this, the measuring portion (160) may include at least one selected from the group consisting of a plurality of electrodes to be adhered to a first area of brain, a current-voltage converter which converts the current signal measured by a plurality of electrodes to the voltage signal, an amplifier which amplifies the voltage signal, a filter which removes noise from the amplified voltage signal, and an A/D (analog to digital) converter which converts the analog signal of the noise-removed voltage signal to the digital signal.

A measuring portion (160) may include at least one selected from the group consisting of a ground electrode, a reference electrode, and a measuring electrode.

A ground electrode can perform the role of matching the reference potential of the first electrical stimulation apparatus (100) with that of a human body. The ground electrode can be adhered to the area where the brainwave signal is not measured or weak, such as the root of the right ear.

Likewise, a reference electrode can be adhered to the area where the brainwave signal is weak or not measured. For example, the reference electrode can be adhered to the same area with the ground electrode is. For another example, the reference electrode can be adhered to a different area from the ground electrode. More particularly, in case the ground electrode is adhered to the root of the right ear, the reference electrode can be adhered to the root of the left ear, back of neck, or a cheek.

A measuring electrode, an active electrode for measuring the brainwave signal of the first user (U1), can be adhered to scalp of the first user (U1). A plurality of such measuring electrodes can be arranged.

A stimulating portion (150) can apply the electrical stimulation to the first user (U1)'s brain. In order for this, the stimulating portion (150) may include a plurality of stimulating electrodes to be adhered to the second area of the brain and a voltage supply portion which provides voltage to a plurality of the stimulating electrodes. At this, the second area and the first area may be either the same or different.

A plurality of the stimulating electrodes may include a positive and a negative electrode. When the voltage is applied to positive and negative electrodes by the voltage supply portion, the electrical current begins to flow between the positive electrode and the negative electrode. Thus, the current reaches to the inside of the first user (U1)'s brain over the network of cranial nerves.

Meanwhile, the voltage supply portion applied the voltage to a plurality of the stimulating electrodes according to a control signal. The control signal can be generated by a control portion (140) which follows, according to the information on the brain activation pattern of the second user (U2).

A control portion (140) can connect and control each element of the first electrical stimulation apparatus (100). According to the exemplary embodiment, the control portion (140) may include an analysis portion (143) and a generating portion (141).

An analysis portion (143) can recognize the brain activation pattern of the first user (U1) by analyzing the first user (U1)'s brainwave signal measured by the measuring portion (160). For example, the analysis portion (143) can perform the analysis of Power Spectrum by using Fast Fourier transform (FFT).

The brainwave signal can be classified according to fluency as such: delta wave (δ wave), theta wave (θ wave), alpha wave (α wave), beta wave (β wave), and gamma wave (γ wave).

The delta wave has a frequency of 0~4 Hz, and is also called 'sleep wave'. The theta wave has a frequency of 4~8 Hz, and is called 'sleepiness wave' or 'slow-wave sleep wave'. The alpha wave has a frequency of 8~13 Hz. The alpha wave is a brainwave generated in physical and mental stability, and is called 'stability wave'. The beta wave has a frequency of 13~30 Hz, and also called 'stress wave'. And the gamma wave has a frequency of 30~50 Hz.

By conducting the Fast Fourier Transform (FFT) of such brainwave signal, the power spectrum showing entire distribution of the power for each frequency ingredient can be obtained. The analysis portion (143), on the basis of the power spectrum, can recognize the brain activation pattern of the first user (U1). That is, the analysis portion (143) can recognize the brain activation pattern of the first user (U1) by analyzing each power value of the delta wave, theta wave, alpha wave, beta wave, and gamma wave in the power spectrum. For example, the analysis portion (143) can analyze the absolute power value of each wave. For another example, the analysis portion (143) can analyze the relative power value of each wave.

A generating portion (141) can generate a control signal necessary for operation of the first electrical stimulation apparatus (100). For example, the generating portion (141) can generate the control signal for applying the electrical stimulation to the first user (U1)'s brain by the stimulating portion (150). The generated control signal can be provided to the stimulating portion (150). Such control signal can be generated when the information on the brain activation pattern of the second user (U2) is received from the second electrical stimulation apparatus (200).

A memory (170) can save the data or algorithm necessary for operation of the first electrical stimulation apparatus (100). For example, the memory (170) can save the data or algorithm necessary for analysis of the brainwave signal of the first user (U1). Besides, the memory (170) can also save the brainwave signal measured by the measuring portion (160) and/or the information on the brain activation pattern of the second user (U2) received from the second electrical stimulation apparatus (200). Such memory (170) can be embodied as non-volatile memory, volatile memory, or the combination thereof.

A communication portion (180) can transmit and receive the signal and/or data to/from the second electrical stimulation apparatus (200). For example, the communication portion (180) can communicate with the second electrical stimulation apparatus (200) by wired or wireless method of communication. The examples of the wired communication method include Ultra-wideband (UWB), Near Field Communication (NFC), Zigbee, WiFi, and Bluetooth, but the example is not limited thereto.

Figure 3:
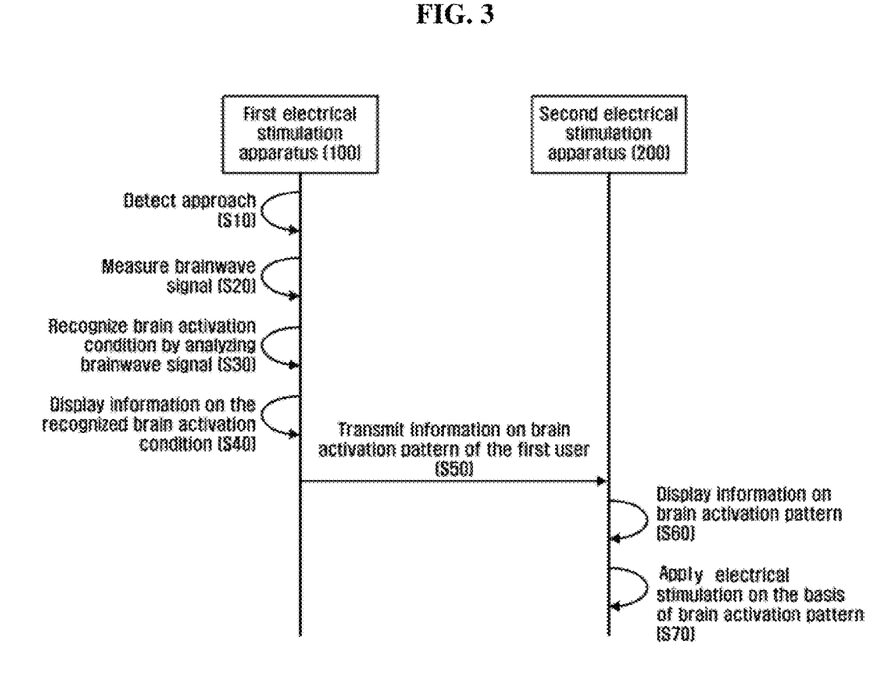
FIG. 3 is a flow chart illustrating a method for electrical stimulation by the electrical stimulation system of FIG. 1.

FIG. 3 is a flow chart illustrating a method for electrical stimulation by the electrical stimulation system of FIG. 1.

First of all, the detecting portion (130) of the first electrical stimulation apparatus (100) detects (S10) the second user (U2) approaching.

The second user (U2)'s approach detected, the measuring portion (160) of the first electrical apparatus (100) measures (S20) the brainwave of the first user (U1).

The brainwave signal measured, the analysis portion (143) of the first electrical stimulation apparatus (100) recognizes (S30) the brain activation pattern of the first user (U1) by analyzing the measured brainwave signal. The above mentioned stage (S30) may include a stage wherein the power spectrum about the brainwave signal is obtained by conducting Fast Fourier Transform (FFT) of the measured brainwave signal, and a stage wherein the power value of each frequency ingredient in the power spectrum is analyzed, and the brain activation pattern of the first user (U1) is recognized.

Once the brain activation pattern of the first user (U1) recognized, the display portion (120) of the first electrical stimulation apparatus (100) displays (S40) the information on the recognized brain activation pattern of the first user (U1). The information on the brain activation pattern of the first user (U1) can be visually and/or auditorily displayed. According to another exemplary embodiment, the stage for displaying the brain activation pattern of the first user (U1) on the first electrical stimulation apparatus (100) can be omitted.

Next, the communication portion (180) of the first electrical stimulation apparatus (100) transmits (S50) the information on the brain activation pattern of the first user (U1) to the second electrical stimulation apparatus (200).

The second electrical simulation apparatus (200) can display (S60) the information on the brain activation pattern of the first user (U1) received from the first electrical stimulation apparatus (100). According to another exemplary embodiment, the stage for displaying the information on the brain activation pattern of the first user (U1) on the second electrical stimulation apparatus (200) can be omitted.

Next, the second electrical stimulation apparatus (200) applies (S70) the electrical stimulation on the basis of the brain activation pattern of the first user (U1) to the brain of the second user (U2). That is, the second electrical stimulation apparatus (200) applies the electrical stimulation, which can activate the brain of the second user (U2) to the condition corresponding to the information on the brain activation pattern of the first user (U1), to be applied to the brain of the second user (U2). As a result, the effect in a way that the emotion of the first user (U1) is transmitted to the second user (U2) can be achieved.

Above, the electrical stimulation method was explained in reference with FIG. 3. FIG. 3 shows the case that the first electrical stimulation apparatus (100) is the main agent recognizing the brain activation pattern of the first user (U1) by analyzing the brainwave signal of the first user (U1). According to another exemplary embodiment, the main agent recognizing the brain activation pattern of the first user (U1) by analyzing the brainwave signal of the first user (U1) can be the second electrical stimulation apparatus (200). In this case, the first electrical stimulation apparatus (100) measures the brainwave signal of the first user (U1) and transmits the result to the second electrical stimulation apparatus (200), and the second electrical stimulation apparatus (200) can recognize the brain activation pattern of the first user (U1) by analyzing the brainwave signal of the first user (U1) received from the first electrical stimulation apparatus (100)

Figure 4:
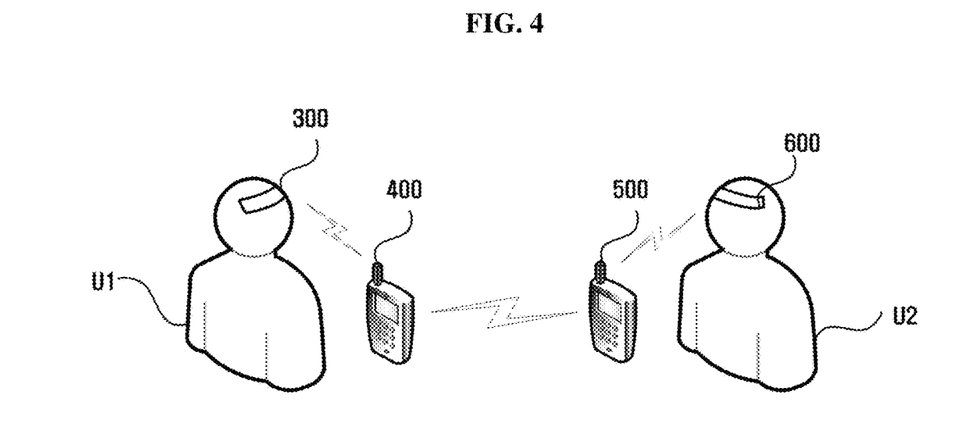
FIG. 4 is a diagram illustrating a composition of the electrical stimulation system according to another exemplary embodiment.

FIG. 4 is a diagram illustrating a composition of the electrical stimulation system according to another exemplary embodiment.

In reference with FIG. 4, the electrical stimulation system may include a first electrical stimulation apparatus (300), a first portable apparatus (400), a second portable apparatus (500), and a second electrical stimulation apparatus (600). The first electrical stimulation apparatus (300) and the second electrical stimulation apparatus (600) may have the same composition. And the first portable apparatus (400) and the second portable apparatus (500) may also have the same composition. Therefore, the explanation which follows will be mainly about the first electrical stimulation apparatus (300) and the first portable apparatus (400).

A first electrical stimulation apparatus (300) is an apparatus wearable on the head of the first user (U1). The pairing process may be performed between the first electrical stimulation apparatus (300) and the first portable apparatus (400). Pairing is a process wherein the information of the first electrical stimulation apparatus (300) is registered in the first portable apparatus (400), and vice versa. For example, the pairing process between the first electrical stimulation apparatus (300) and the first portable apparatus (400) can be performed by the method of Bluetooth or Near Field Communication (NFC).

The first electrical stimulation apparatus (300) can measure the brainwave signal of the first user (U1) when the result of detection of the second user (U2)'s approach is transmitted from the first portable apparatus (400). The measured brainwave signal can be transmitted to the first portable apparatus (400). More details about the composition of the first electrical stimulation apparatus (300) will be explained thereinafter in reference with FIG. 5.

A first portable apparatus (400) is a portable apparatus possessed by the first user (U1). As previously explained, the pairing process can be performed between the first portable apparatus (400) and the first electrical stimulation apparatus (300).

Such first portable apparatus (400) can detect the second user (U2) approaching, and transmit the result of detection to the first electrical stimulation apparatus (300). As a result, the first portable apparatus (400) can receive the brainwave signal from the first electrical stimulation apparatus (300). And the first portable apparatus (400) can recognize the brain activation pattern of the first user (U1) by analyzing the received brainwave signal, and generate the control signal on the basis of the information on the recognized brain activation pattern of the first user (U1). The first portable apparatus (400) can transmit the generated control signal and the information on the recognized brain activation pattern of the first user (U1) to the second portable apparatus (500). More details about the composition of the first portable apparatus (400) will be described thereinafter in reference with FIG. 6.

A second portable apparatus (500) is a portable apparatus possessed by the second user (U2). The pairing process between the second portable apparatus (500) and the second electrical stimulation apparatus (600) can be performed. For example, the first electrical stimulation apparatus (300) and the first portable apparatus (400) can perform pairing process by using the methods of Bluetooth or Near Field Communication (NFC). The pairing process finished, the information of the second portable apparatus (500) is registered on the second electrical stimulation apparatus (600), and vice versa.

Such second portable apparatus (500) can receive the information on the brain activation pattern of the first user (U1) and the control signal from the first portable apparatus (400). In addition, the second portable apparatus (500) can display the information of the received brain activation pattern of the first user (U1), and transmit the received control signal to the second electrical stimulation apparatus (600).

A second electrical stimulation apparatus (600) is an apparatus wearable on the head of the second user (U2). As previously explained, the pairing process can be performed between the second electrical stimulation apparatus (600) and the second portable apparatus (500). The second electrical stimulation apparatus (600) can apply the electrical stimulation to the brain of the second user (U2) according to the control signal received from the second portable apparatus (500).

Figure 5:
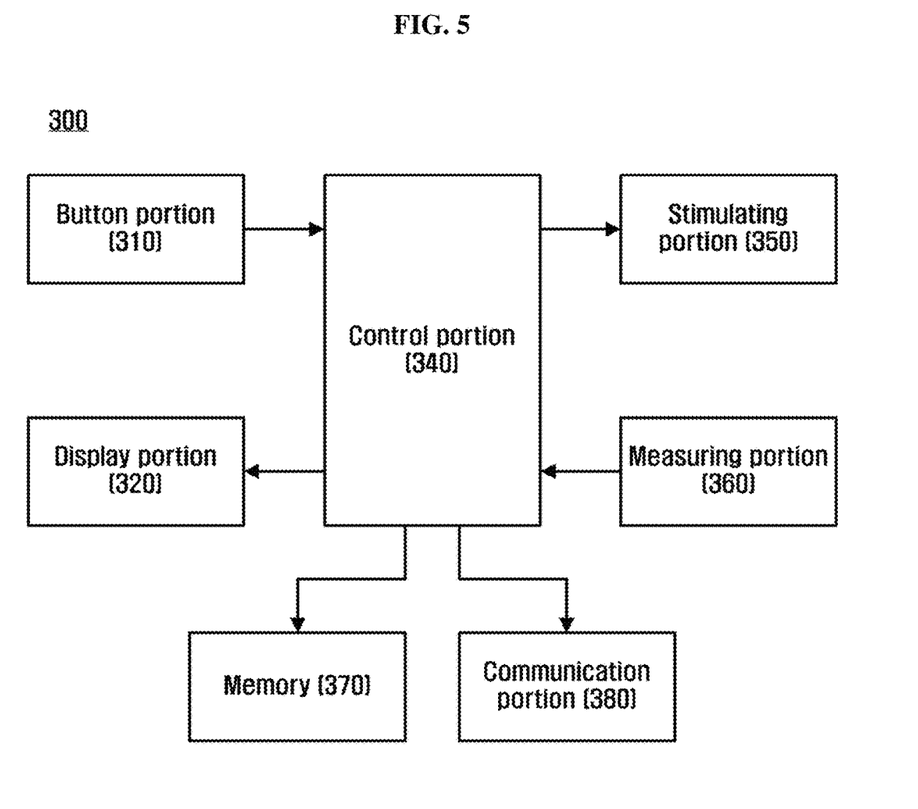
FIG. 5 is a diagram illustrating a composition of the first electrical stimulation apparatus (300) of FIG. 4.

FIG. 5 is a diagram illustrating a composition of the first electrical stimulation apparatus (300) of FIG. 4.

In reference with FIG. 5, the first electrical stimulation apparatus (300) may include a button portion (310), a display portion (320), a control portion (340), a stimulating portion (350), a measuring portion (360), a memory (370), and a communication portion (380). The button portion (310), the display portion (320), the stimulating portion (350), the measuring portion (360), and the memory (370) of FIG. 5 is similar or same with the button portion (110), the display portion (120), the stimulating portion (150), the measuring portion (160), and the memory (170) of FIG. 2; thus, the repetitive explanation thereof will be omitted.

A communication portion (380) can transmit and receive the data and/or the signal to/from the first portable apparatus (400) by the method of wired or wireless communication. For example, the communication portion (380) can receive the result of detection of the second user (U2)'s approach from the first portable apparatus (400). In addition, the communication potion (380) can transmit the brainwave signal of the first user (U1) measured by the measuring portion (360) to the first portable apparatus (400).

A memory (370) can save the brainwave signal measured by the measuring portion (360). Such memory (370) can be embodied as a non-volatile memory (370), a volatile memory (370), or the combination thereof.

A control portion (340) can connect and control each element of the first electrical stimulation apparatus (300). For example, in case the result of detection of the second user (U2)'s approach received from the first portable apparatus (400), the control portion (340) can control the measuring portion (140) to measure the brainwave signal of the first user (U1). While the control portion (140) of FIG. 2 includes the generating portion (141) and the analysis portion (143), they are omitted in the control portion (340) of FIG. 5

Figure 6:
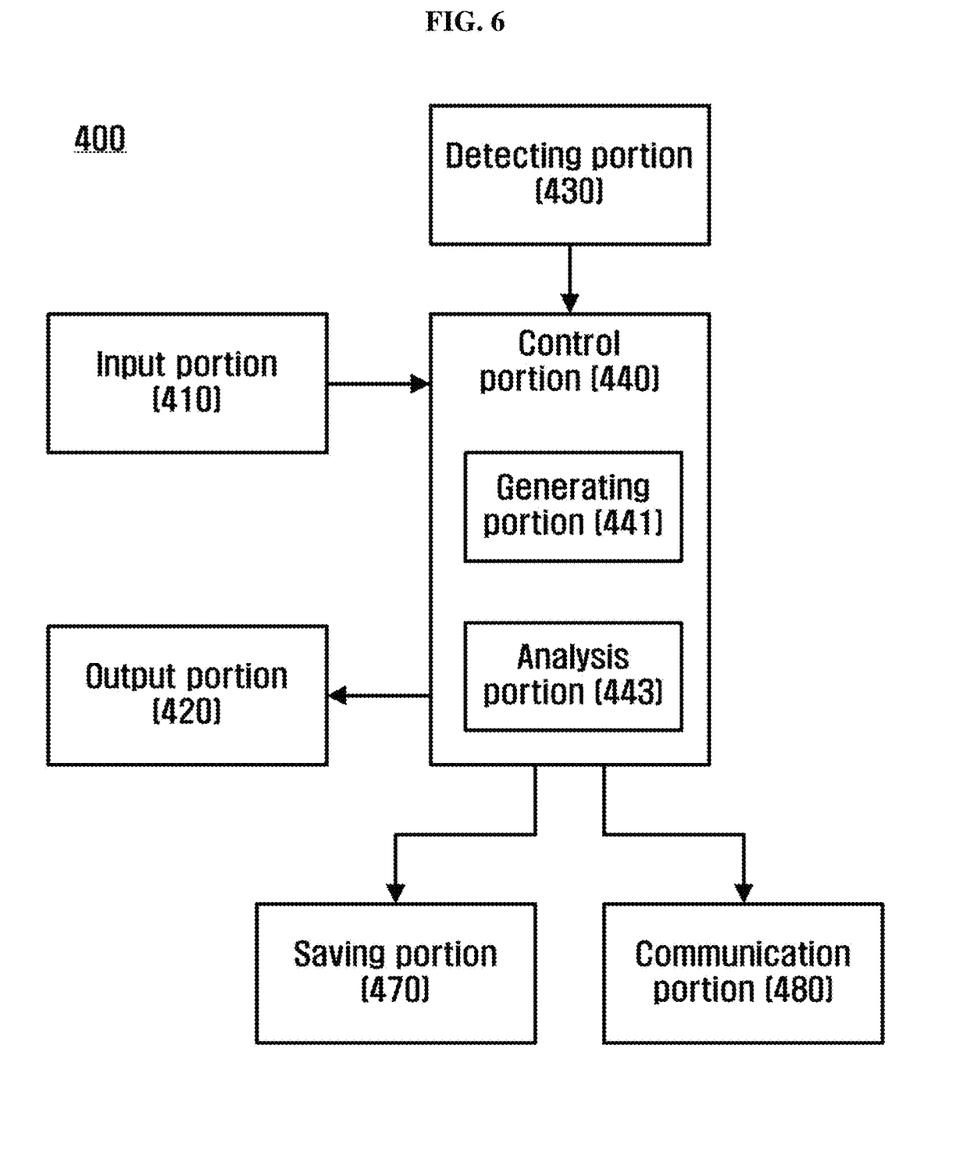
FIG. 6 is a diagram illustrating a composition of the first portable apparatus (400) of FIG. 4.

FIG. 6 is a diagram illustrating a composition of the first portable apparatus (400) of FIG. 4.

In reference with FIG. 6, the first portable apparatus (400) may include an input portion (410), an output portion (420), a detecting portion (430), a control portion (440), a saving portion (470), and a communication portion (480).

An input portion (410) may receive a command of the first user (U1). In order for this, the input portion (410) may include at least one key.

An output portion (420) can output the result of processing the command as auditory and/or visual signal. For example, the output portion (420) can output, as a result of detection of the second user (U2)s approach, at least one selected between the brainwave signal of the first user (U1) received from the first electrical stimulation apparatus (300) and the information on the brain activation pattern of the first user (U1) obtained by the first brainwave signal. Such output portion (420) can be embodied as LCD, or flexible LCD. For example, the output portion (420) may have an output function only. For another example, the output portion (420) may have both output and input functions, such as touch screen.

A detecting portion (430) can detect the approach of the second user (U2). The detecting portion (430) may include a distance sensor or a motion detecting sensor. The result of detection by the detecting portion can be transmitted to the first electrical apparatus (300), and used as an event signal for notifying the start of measuring the brainwave signal of the first user (U1).

A control portion (440) can connect and control each element of the first portable apparatus (400). According to the exemplary embodiment, the control portion (440) may include a generating portion (441) and an analysis portion (443).

An analysis portion (443) can recognize the brain activation pattern of the first user (U1) by analyzing the brainwave signal of the first user (U1) measured by the first electrical stimulation apparatus (300). Particularly, the analysis portion (443) can perform the power spectrum analysis by using the Fast Fourier Transform (FFT). For example, the analysis portion (443) can recognize the brain activation pattern of the first user (U1) by comparing the absolute power value of each frequency element with the previously saved reference power values. For another example, the analysis portion (443) can recognize the brain activation pattern of the first user (U1) by analyzing the relative power value of each frequency element. The recognized brain activation pattern of the first user (U1) can be transmitted to the second portable apparatus (500).

A generating portion (441) can generate the control signal for applying the electrical stimulation corresponding to the brain activation pattern of the first user (U1) to the brain of the second user (U2). The generated control signal, for example, may include at least one selected between the information on the strength and the time for the electrical stimulation to be applied to the brain of the second user (U2). The control signal generated from the generating portion (441) can be transmitted to the second portable apparatus (500).

A saving portion (470) can save the data or algorithm necessary for the operation of the first portable apparatus (400). For example, the saving portion (470) can save the data or algorithm necessary for analyzing the brainwave signal of the first user (U1) measured by the first electrical stimulation apparatus (300). Particularly, the saving portion (470) can save the algorithm for the Fast Fourier Transform of the brainwave signal, and the reference power values to be compared with the power value of each frequency element in the power spectrum obtained by the Fast Fourier Transform (FFT). Such saving portion (470) may include a non-volatile memory, a volatile memory, a hard disk drive, an optical disk drive, or the combination thereof.

A communication portion (480) can communicate with the first electrical stimulation apparatus (300) and the second portable apparatus (500) by wired or wireless method of communication. For example, the communication portion (480) can transmit the result of detection of the second user (U2)'s approach to the first electrical stimulation apparatus (300), and receive the brainwave signal of the first user (U1) from the first electrical stimulation apparatus (300). In addition, the communication portion (480) can transmit the information on the brain activation pattern of the first user (U1) and/or the control signal on the basis of the information thereof to the second portable apparatus (500).

The first portable apparatus (400) described above may include a wired and wireless communication device. The examples of the communication device include a mobile device such as a Cellular phone, a PCS phone (Personal Communications Service phone), and a synchronous/asynchronous IMT-2000 (International Mobile Telecommunication-2000), a Palm PC (Personal Computer), a PDA (Personal Digital Assistant), a Smart phone, a WAP phone (Wireless application protocol phone), and a mobile playstation.

Figure 7:
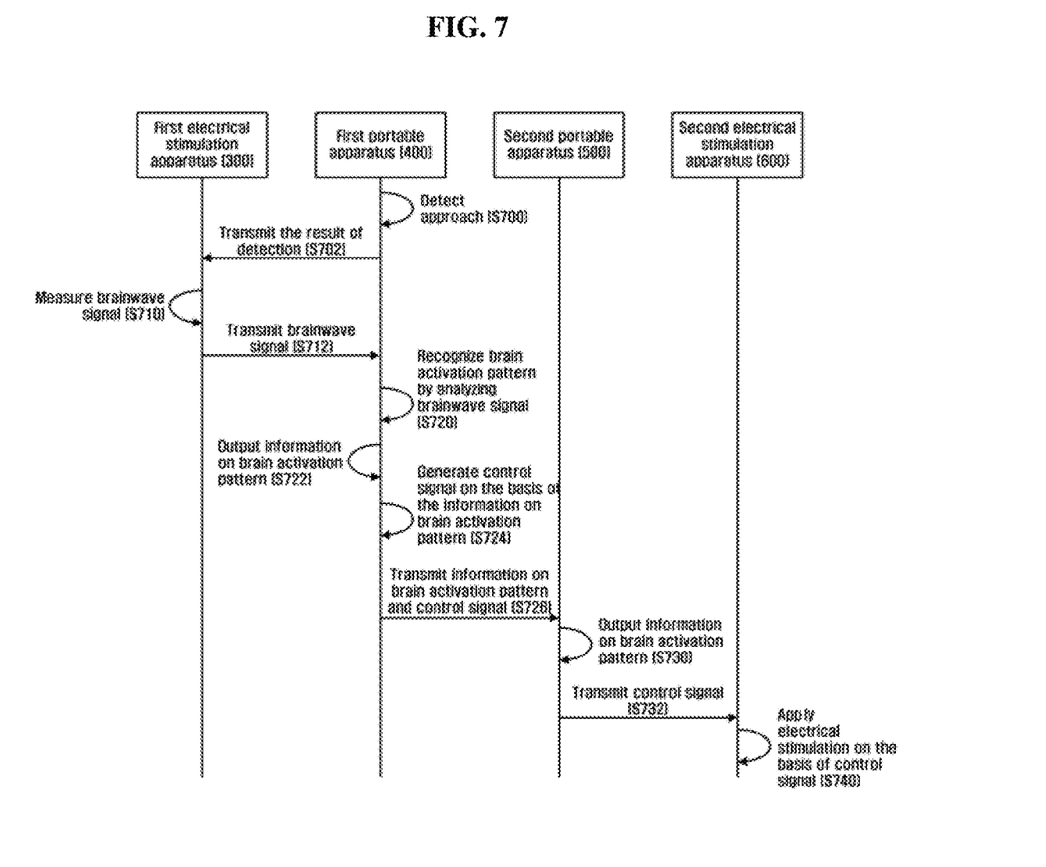
FIG. 7 is a flow chart illustrating one exemplary embodiment of the electrical stimulation method on the basis of the electrical stimulation system of FIG. 4.

FIG. 7 is a flow chart illustrating one exemplary embodiment of the electrical stimulation method on the basis of the electrical stimulation system of FIG. 4.

First of all, the detecting portion (430) of the first portable apparatus (400) detects (S700) the second user (U2) approaching, and transmits (S702) the result of detection to the first electrical stimulation apparatus (300).

Next, the measuring portion (360) of the first electrical stimulation apparatus (300) measures (S710) the brainwave signal of the first user (U1), and transmits (S712) the measured brainwave signal to the first portable apparatus (400).

Once the brainwave signal of the first user (U1) received, the analysis portion (443) of the first portable apparatus (400) recognizes (S720) the brain activation pattern of the first user (U1) by analyzing the received brainwave signal of the first user (U1). The above mentioned stage (S720) may include a stage wherein the power spectrum about the brainwave signal is obtained by conducting Fast Fourier Transform (FFT) of the brainwave signal of the first user (U1), and a stage wherein the power value of each frequency element in the power spectrum is analyzed, and the brain activation pattern of the first user (U1) is recognized.

Once the brain activation pattern of the first user (U1) recognized, the output portion (420) of the first portable apparatus (400) outputs (S722) the recognized brain activation pattern of the first user (U1) as an auditory and/or visual signal. According to another exemplary embodiment, the stage (722) for outputting the brain activation pattern of the first user (U1) can be omitted.

In addition, the generating portion (441) of the first portable apparatus (400) can generate (S724) the control signal on the basis of the information on the brain activation pattern of the first user (U1). The above mentioned control signal may be a control signal for applying the electrical stimulation corresponding to the information on the brain activation pattern of the first user (U1) to be applied to the brain of the second user (U2) by the second electrical stimulation apparatus (600).

Next, the first portable apparatus (400) can transmit (S726) the information on the brain activation pattern of the first user (U1) and the generated control signal to the second portable apparatus (500).

Then, the second portable apparatus (500) outputs (S730) the information on the brain activation pattern of the first user (U1) received from the first portable apparatus (400) as an auditory and/or visual signal, and transmits (S732) the received control signal to the second electrical stimulation apparatus (600). According to another exemplary embodiment, the stage for outputting the information on the brain activation pattern of the first user (U1) on the second portable apparatus (500) can be omitted.

Figure 8:
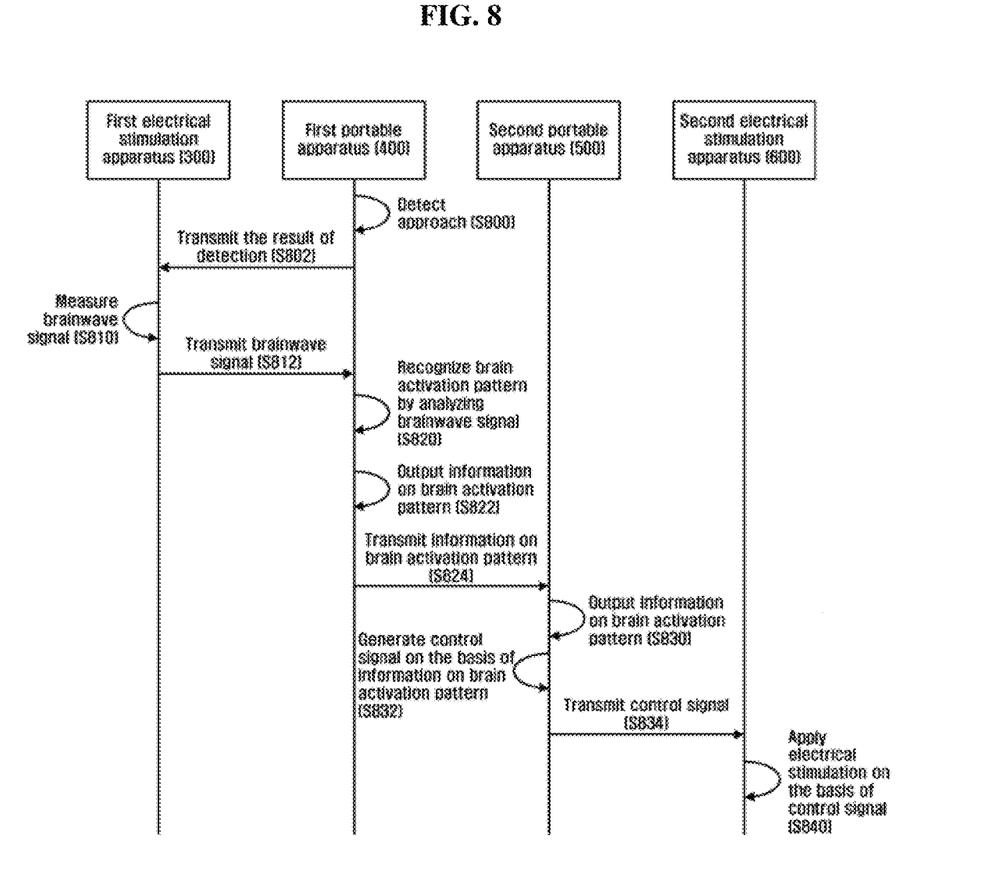
FIG. 8 is a flow chart illustrating another exemplary embodiment of the electrical stimulation method according to the electrical stimulation system of FIG. 4.

The second electrical stimulation apparatus (600) receives the control signal from the second portable apparatus (500), and applies (S740) the electrical stimulation on the basis of the received control signal to the brain of the second user (U2). As a result, the brain condition of the second user (U2) can be activated to become similar with that of the first user (U1). That is, the effect in a way that the emotion of the first user (U1) is transmitted to the second user (U2) can be achieved FIG. 8 is a flow chart illustrating another exemplary embodiment of the electrical stimulation method according to the electrical stimulation system of FIG. 4.

First of all, the detecting portion (430) of the first portable apparatus (400) detects (S800) the approach of the second user (U2), and transmits (S802) the result of detection to the first electrical stimulation apparatus (300).

After this, the measuring portion (360) of the first electrical stimulation apparatus (300) measures (S810) the brainwave signal of the first user (U1), and transmits (S812) the measured brainwave signal to the first portable apparatus (400).

The brainwave signal of the first user (U1) received, the analysis portion (443) of the first portable apparatus (400) recognizes (S820) the brain activation pattern of the first user (U1) by analyzing the received brainwave signal of the first user (U1). The above mentioned stage (S820) may include a stage wherein the power spectrum about the brainwave signal is obtained by conducting Fast Fourier Transform (FFT) of the brainwave signal of the first user (U1), and a stage wherein the power value of each frequency element in the power spectrum is analyzed, and the brain activation pattern of the first user (U1) is recognized.

For example, when the power value of each frequency element in the power spectrum is analyzed, the power value of each frequency element is compared with the reference power values previously saved, and the brain activation pattern of the first user (U1) can be recognized. For another example, when the power value of each frequency element of the power spectrum is analyzed, by the relative power value of each frequency element being analyzed, the brain activation pattern of the first user (U1) can be recognized.

The brain activation pattern of the first user (U1) recognized, the output portion (420) of the first portable apparatus (400) outputs (S822) the information of the brain activation pattern of the first user (U1) as an auditory and/or visual signal. According to another exemplary embodiment, the stage (S822) for outputting the information on the brain activation pattern of the first user (U1) on the first portable apparatus (400) can be omitted.

Next, the communication portion (480) of the first portable apparatus (400) transmits (S824) the information on the recognized brain activation pattern of the first user (U1) to the second portable apparatus (500).

The second portable apparatus (500) outputs (S830) the information on the brain activation pattern of the first user (U1) received from the first portable apparatus (400) as an auditory and/or visual signal. According to another exemplary embodiment, the stage (S830) for outputting the brain activation pattern of the second user (U2) on the second portable apparatus (500) can be omitted.

Next, the second portable apparatus (500) can generate (S832) the control signal on the basis of the information on the brain activation pattern of the first user (U1). The above mentioned control signal can be a control signal for applying the electrical stimulation on the basis of the brain activation pattern of the first user (U1) to be applied to the brain of the second user (U2) by the second electrical stimulation apparatus (600).

Then, the second portable apparatus (500) transmits (S834) the generated control signal to the second electrical stimulation apparatus (600).

The second electrical stimulation apparatus (600) receives the control signal from the second portable apparatus (500), and applies (S840) the electrical stimulation on the basis of the received control signal to be applied to the brain of the second user (U2). As a result, the brain condition of the second user (U2) can be activated to become similar with that of the first user (U1). That is, the effect in a way that the emotion of the first user (U1) is transmitted to the second user (U2) can be achieved.

Above, the exemplary embodiments of the present invention have been described. In addition to the exemplary embodiments previously described, the exemplary embodiments of the present invention can be embodied with a medium including a computer readable code/command, such as a computer readable medium, in order to control at least one processing element of the exemplary embodiments previously described. The medium can correspond to a medium/media enabling the saving and/or transmission of the computer readable code.

The above mentioned computer readable code can be transmitted via internet as well as recorded on a medium. The example of the medium may include a recording medium such as magnetic storing medium (for example, ROM, floppy disk, hard disk) and an optical recording medium (for example, CD-ROM, Blu-Ray, DVD), and a transmission medium such as a carrier wave. The above mentioned media may be a distribution network; thus, the computer readable code can be saved/transmitted and operated by means of distribution. Moreover, for example, the processing element may include a processor or a computer processor, and the above mentioned processing element can be distributed and/or included in a single device.

It is clearly understandable for those having ordinary skill in the art the present invention can be embodied in various forms, other than the exemplary embodiments set forth herein, without changes in its technical idea or essential characteristic. The exemplary embodiments described herein are only for the purpose of exemplifying the present invention in all aspects, not of limiting the scope of the present invention.

DESCRIPTION FOR REFERENCE NUMERALS 100, 300: First electrical stimulation apparatus
200, 600: Second electrical stimulation apparatus
400: First portable apparatus
500: Second portable apparatus

The invention claimed is:
1. An electrical stimulation system, comprising
an analysis portion recognizing the emotion of a first user by analyzing a brainwave signal of a first user measured by a first electrical stimulation apparatus;

and a stimulating portion applying the electrical stimulation to the brain of a second user on the basis of the information on the recognized emotion of the first user, wherein the analysis portion is included in a second electrical stimulation apparatus different from the first electrical stimulation apparatus.

2. According to claim 1, the electrical stimulation system, wherein the second electrical stimulation apparatus further includes a display portion displaying the information on the brain activation pattern of the first user.

3. An electrical stimulation system, comprising

An analysis portion recognizing the emotion of a first user by analyzing a brainwave signal of the first user measured by a first electrical stimulation apparatus; and a stimulating portion applying an electrical stimulation to the brain of a second user on the basis of the information on the recognized emotion of the first user, wherein the analysis portion is included in a first portable apparatus paired with the first electrical stimulation apparatus.

4. An electrical stimulation system, comprising an analysis portion recognizing the emotion of a first user by analyzing a brainwave signal of the first user measured by a first electrical stimulation apparatus; and a stimulating portion applying an electrical stimulation to the brain of a second user on the basis of the information on the recognized emotion of the first user, wherein the analysis portion is included in a second portable apparatus paired with a second electrical stimulation apparatus different from the first electrical stimulation apparatus.

* * * * *